United States Patent
Domen et al.

(10) Patent No.: US 8,323,611 B2
(45) Date of Patent: Dec. 4, 2012

(54) SOLID ACID CATALYST

(75) Inventors: Kazunari Domen, Kanagawa (JP); Michikazu Hara, Kanagawa (JP)

(73) Assignee: Japan Science and Technology Agency, Saitama-ken (JP)

( * ) Notice: Subject to any disclaimer, the term of this patent is extended or adjusted under 35 U.S.C. 154(b) by 1842 days.

(21) Appl. No.: 10/533,567

(22) PCT Filed: Jun. 16, 2003

(86) PCT No.: PCT/JP03/07614
§ 371 (c)(1), (2), (4) Date: May 3, 2005

(87) PCT Pub. No.: WO2004/047982
PCT Pub. Date: Jun. 10, 2004

(65) Prior Publication Data
US 2006/0058186 A1    Mar. 16, 2006

(30) Foreign Application Priority Data

Nov. 25, 2002  (JP) ................................ 2002-340340

(51) Int. Cl.
*C01G 31/02* (2006.01)
*C01G 33/00* (2006.01)
*C01G 23/00* (2006.01)

(52) U.S. Cl. ..................................... 423/594.8; 423/598

(58) Field of Classification Search .................. 423/598, 423/594.8
See application file for complete search history.

(56) References Cited

OTHER PUBLICATIONS

Yoshida, et al., "Shinki 2-jigen Kotaisan Sen'i Kinzoku Sankabutsu Sheet ni yoru Shokubai Hanno no Kento", CSJ:The Chemical Society of Japan Dai 81 Shunki Nenkai-Koen Yokoshu I, Mar. 11, 2002.
Hara, et al., "Kotaisan to shite no Kinzoku Sankabutsu Nano Sheet", Shokubai, Jun. 10, 2002, vol. 44, No. 4.
Takagaki, et al., "Titan Niobate Sankabutsu Sheet no Kozo to Kotai Sansei", Dai 90 kai Shokubai Toronkai A Yokoshu, Sep. 10, 2002.
Ishihara, et al., Polystyrene-Bound Tetrafluorophenylbis(triflyl)methane as an Organic-Solvent-Swellable and Strong Bronsted Acid Catalyst, Angew. Chem. Int. Ed. 2001, 40, No. 21.

*Primary Examiner* — Stanley Silverman
*Assistant Examiner* — Jennifer Smith
(74) *Attorney, Agent, or Firm* — Hahn & Voight PLLC; Roger C. Hahn

(57) ABSTRACT

A solid acid catalyst represented by $HTi_xNb_yO_5$ wherein x is $1.1<x<1.2$ and y is $0.9>y>0.8$, having a Ti/Nb atomic ratio z of $1<z<1.5$, and has been produced by subjecting a cation exchangable lamellar metal oxide composed of polyanion nano-sheets comprising lamellar metal oxide layers of titanium niobate being arranged regularly while sandwiching an alkali metal cation between them to the proton exchange of the alkali metal cation by the use of an inorganic acid or an organic acid prepared into a 0.0001M to 1M solution, and then inserting a cation selected from the group consisting of an organic amine and an organic ammonium between the resulting proton exchanged layers, to thereby delaminate the laminated layers temporarily and prepare an aqueous colloidal solution comprising metal oxide sheets having the organic amine or organic ammonium adsorbed thereon, and then adding an inorganic acid or an organic acid prepared into a 0.0001M to 1M solution to the colloidal solution, to thereby exchange the organic amine or organic ammonium with a proton and simultaneously coagulate the resulting products onto the titanium niobate nano-sheet.

5 Claims, 2 Drawing Sheets

SOLID ACID CATALYST

FIELD OF THE INVENTION

The present invention relates to a novel solid acid catalyst obtained by using anion nano-sheet comprising lamellar metal oxide layers of titanium niobate containing alkali metal ion as a starting material, changing said sheet to a proton exchanger, cation exchanging said proton exchanger with organic amine or organic ammonium, removing said layers so as to prepare a colloidal solution, then re-coagulating and proton exchanging said colloidal solution by prepared protonic acid, wherein a Ti/Nb atomic ratio z is in the range of $1.1 < z < 1.5$.

DESCRIPTION OF THE PRIOR ART

Realization of chemical synthesis truly harmonized with environment is a fundamental theme for constructing a scientific technique of $21^{st}$ century reconsidering the problems of energy and environment. Mainly, organic reactions which combine carbon with carbon are progressed by Lewis acid catalyst. Among said circumstances, designing and construction of an acid catalyst which proceeds specifically a peculiar reaction in water, which is safe solvent, maintaining an activity of the catalyst is an unavoidable factor for the realization of said theme. Considering said theme, many researchers are concerning with research and development of various Lewis acid catalysts, Brønsted acid catalysts or composite catalysts thereby and earnestly trying to develop a high activated "super acid catalyst". By these developments, catalytic reactions such as ester dehydration condensation or amide dehydration condensation, which were impossible by conventional arts, are realized.

Among these developments, solid acid catalysts such as zeolite or perfluorosulfonic acid resin are paid attention from the views, point that the recovery from a reaction system and reuse are easy, and a "super acid catalyst" characterizing by loading pentafluorophenylbis(trifuril)methane ($C_6F_5CHTf_2$) to polystyrene resin is proposed as a solid catalyst which progresses organic reaction effectively (Ishihara, K; Hasegawa, A; Yamamoto, H. Angew. Chem. Int. Ed. 2001, 40, 4077., Document 1).

On the contrary, the inventors of the present invention have continued the investigation to prepare a solid acid catalyst from polyanion nano-sheet. In "AbstractI" of the $81^{st}$ annual forum of Japan Chemical Society (2002) issued on Mar. 1, 2002, page 165 (3C5-31) (Document 2), a trial of designing of a solid acid catalyst which uses polyanion nano-sheet and the structure of which is controlled in nano level by constructing a self-organized macro molecule and by which liquid phase esterfication reaction can be specifically controlled is tried. However, in this trial, only a solid acid catalyst obtained by removing, re-coagulating lamellar metal oxide of Ti/Nb=1 and Ti/Nb=2 is proposed, and in the trial, the element ratio of Ti/Nb and activity of solid acid catalyst, especially the activity in liquid phase esterfication reaction are not referred at all. Further, in "Abstract of Session A" of the $90^{th}$ Catalyst Forum of Catalyst Society issued on Sep. 10, 2002, page 183 (4E09) (Document 3), the element ratio of Ti/Nb and activity of solid acid catalyst are referred, and in said document, it is reported that the catalyst is more activated at Ti/Nb=0.818, which is smaller value than 1.

The subject of the present invention is to provide a high effective solid acid catalyst which is active than the proposed solid acid catalyst mentioned above using a polyanion nano-sheet having alkali metal cation between layers, in particular, using a lamellar metal oxide containing titanium, niobium and alkali metal. For dissolving said subject, the inventors of the present invention have carried out various experiments by trial and error as follows. That is, a lamellar metal oxide containing titanium, niobium and alkali metal in which blending ratio of titanium a niobium is changed is synthesized, then the resulting lamellar metal oxide is cation exchanged with organic amine or organic ammonium and layers are re-laminated. Two dimensional re-coagulated sheet is prepared by adding acid and a liquid esterfication reaction is tried using said two dimensional re-coagulated sheet, and it is confirmed that very activated solid acid catalyst can be obtained at Ti/Nb ratio z is $1 < z < 1.5$, especially at z is $1.2 < z < 1.4$, thus the subject of the present invention is dissolved.

SUMMARY OF THE INVENTION

The first one of the present invention is, (1) a solid acid catalyst represented by $HTi_xNb_yO_5$, wherein x is $1.1 < x < 1.2$ and y is $0.9 > y > 0.8$, having a Ti/Nb atomic ratio z of $1 < z < 1.5$, obtained by proton changing of alkali metal cation of cation changeable lamellar metal oxide in which polyanion nano-sheet comprising lamellar metal oxide layers of titanium niobate lying alkali metal cation between are regularly laminated by inorganic acid or organic acid adjusted to 0.0001M to 1M, delaminating said laminated layers temporarily by inserting cation selected from the group consisting of organic amine or organic ammonium between layers of proton exchangers, preparing an aqueous colloidal solution comprising metal oxide sheets to which said organic amine or organic ammonium is absorbed, then proton exchanging said organic amine or organic ammonium by adding inorganic acid or organic acid adjusted to 0.0001M to 1M to said aqueous colloidal solution and simultaneously coagulating on titanium niobate nano-sheet. Desirably, the first one of the present invention is (2) the solid acid catalyst of (1), wherein a Ti/Nb atomic ratio z is $1.2 < z < 1.4$, more desirably the first one of the present invention is (3) the solid acid catalyst of (1) or (2), wherein organic amine or organic ammonium is at least one selected from the group consisting of ethylamine, propylamine or tetrabutylammonium. Further desirably, the first one of the present invention is (4) the solid acid catalyst of (1), (2) or (3), wherein the surface area of coagulated titanium niobate nano-sheet is 10 times or more to the surface area of cation changeable lamellar metal oxide proton exchanger and is in the range from 60 $m^2g^{-1}$ to 150 $m^2g^{-1}$.

The second one of the present invention is an ester dehydration condensation catalyst composed of the solid acid catalyst of (1) to (4).

BRIEF DESCRIPTION OF THE DRAWINGS

In FIG. 1, 1 is the protonation process which exchanges interlayer ions of lamellar metal oxide with proton in aqueous solution of inorganic acid or organic acid, 2 is a process to prepare re-laminated anion nano-sheets 3 by inserting organic amine or organic ammonium cation between the layers of said lamellar metal oxide proton exchanger and re-laminating and forming colloid so as to prepare re-laminated anion nano-sheet (2 and 3 of FIG. 1). 4 is a process showing to exchange absorbed organic cation with proton by adding inorganic acid or organic acid to said re-laminated colloidal solution and to re-coagulate on the nano-sheet composing solid acid catalyst 5.

DESCRIPTION OF THE PREFERRED EMBOYMENT

Figure 1:
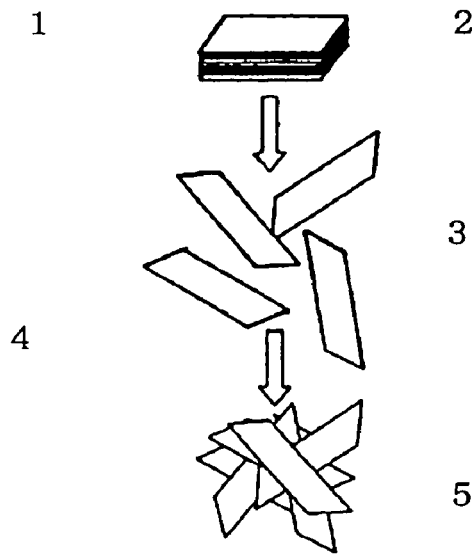
FIG. 1 is the drawing showing the synthesis process of the solid acid catalysts represented by numerical marks from 1 to 5.

The present invention will be illustrated more in detail.
A. The lamellar metal oxide which synthesizes solid acid catalyst of the present invention can be synthesized by baking a precursor comprising salt of Ti or Nb ion or metal ion of alkali metal ion or polymer in air at 500° C.-1500° C.
B. Process for synthesis of solid acid catalyst is shown in FIG. 1. Said process is composed of,
  1. Process to exchange interlayer ions of lamellar metal oxide obtained in said A with protons in inorganic or organic aqueous solution of 0.0001M-1M (1. of FIG. 1),
  2. Process to insert 10 times or less amount of organic amine or organic ammonium cation to the amount of the lamellar metal oxide proton exchanger (2 and 3 of FIG. 1) and forming colloidal solution by re-laminating from cation exchangeable lamellar metal oxide as a colloid to which said organic amine or organic ammonium cation is absorbed (2 and 3 of FIG. 1) and
  3. Process to exchange absorbed organic cations with protons by adding inorganic or organic aqueous solution of 0.0001M-1M to said re-laminated colloidal solution and to coagulate on a titanium niobate nano-sheet (4 of FIG. 4).

Said each process can be progressed in room temperature.
C. As an acid to be used in the protonation process which synthesizes the solid acid catalyst, both inorganic or organic acid can be used.
D. As an organic amine to be used in synthesizing process of the solid acid catalyst, alkyl amines such as ethyl amine, propyl amine or butyl mine can be used. And as an organic ammonium, quaternary alkylammonium cation such as tetrabutylammonium cation or tetraethylammonium cation can be used.

EXAMPLE

The present invention will be illustrated more specifically according to the Examples, however, not intending to limit the scope of the present invention.
Measuring Apparatus;
A. Powder X-ray diffraction spectrum of lamellar metal oxide and synthesized solid acid catalyst are measured by Powder X-ray Diffractometory of Rigaku Co., Ltd.
B. Surface area of synthesized solid acid catalyst is measured by a Surface Area Measuring apparatus of COULTER Co., Ltd.

Example 1

Figure 2:
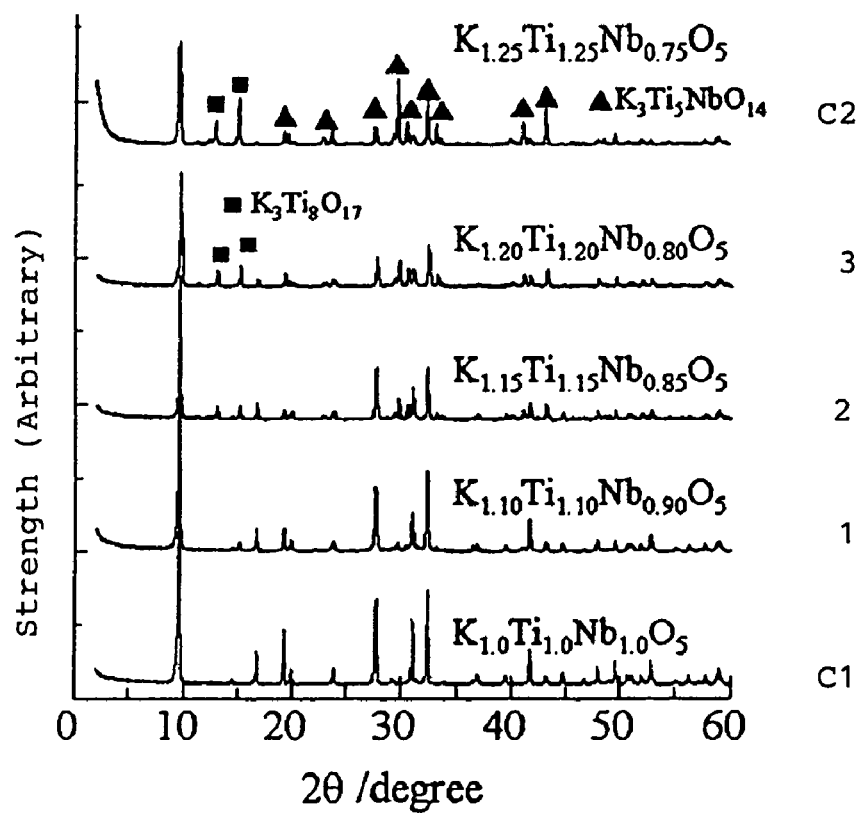
FIG. 2 is the powder X ray diffraction spectrum of lamellar metal oxide for synthesizing solid acid catalyst of Examples 1 and 2 and Comparative Examples 1 and 2 (from the bottom, Comparative Example 1 (1C), Example 1 (1), Example 2 (2) and Comparative Example 2 (2C)) and synthesized solid acid catalysts therefrom.

Powder mixture of $K_2CO_3$, $TiO_2$, $Nb_2O_5$ is prepared by substance ratio 1.1:1.1:0.9, and lamellar metal oxide $K_{1.1}Ti_{1.1}Nb_{0.9}O_5$ is obtained by calcination of the mixture in air at 800° C. for 12 hours. The powder X-ray diffraction spectrum of $K_{1.1}Ti_{1.1}Nb_{0.9}O_5$ is shown in FIG. 2. The surface area of $K_{1.1}Ti_{1.1}Nb_{0.9}O_5$ powder is 1 $m^2g^{-1}$. Powder of lamellar metal oxide proton exchanger of $H_{1.1}Ti_{1.1}Nb_{0.9}O_5$ is obtained by dispersing 2 g of $K_{1.1}Ti_{1.1}Nb_{0.9}O_5$ powder in 200 mL of 1M nitric acid and penetrated for 14 hours then filtrated. 2 g of $H_{1.1}Ti_{1.1}Nb_{0.9}O_5$ powder is dispersed in 150 mL of distilled water and add 15% aqueous solution of tetrabutylammonium hydroxide and bring the pH of the aqueous solution to 8-11 and stirred. During the stirring, pH of aqueous solution is maintained 8-11 by adding 15 wt % of aqueous solution of tetrabutylammonium hydroxide. After stirring of 24 hours, white dispersion is obtained. The obtained dispersion is centrifuged for 10 minutes by 3000 rpm and the colloidal solution of $Ti_{1.1}Nb_{0.9}O_5$ sheet to which tetrabutylammonium cation is absorbed is separated as a supernatant. When 20 mL of 0.1M nitric acid aqueous solution is added to 30 mL of colloidal solution of $Ti_{1.1}Nb_{0.9}O_5$ sheet, the colloid of $Ti_{1.1}Nb_{0.9}O_5$ sheet is precipitated and the coagulation of $H_{1.1}Ti_{1.1}Nb_{0.9}O_5$ sheet is obtained. The surface area of $H_{1.1}Ti_{1.1}Nb_{0.9}O_5$ sheet coagulation is 153 $m^2g^{-1}$.

Figure 3:
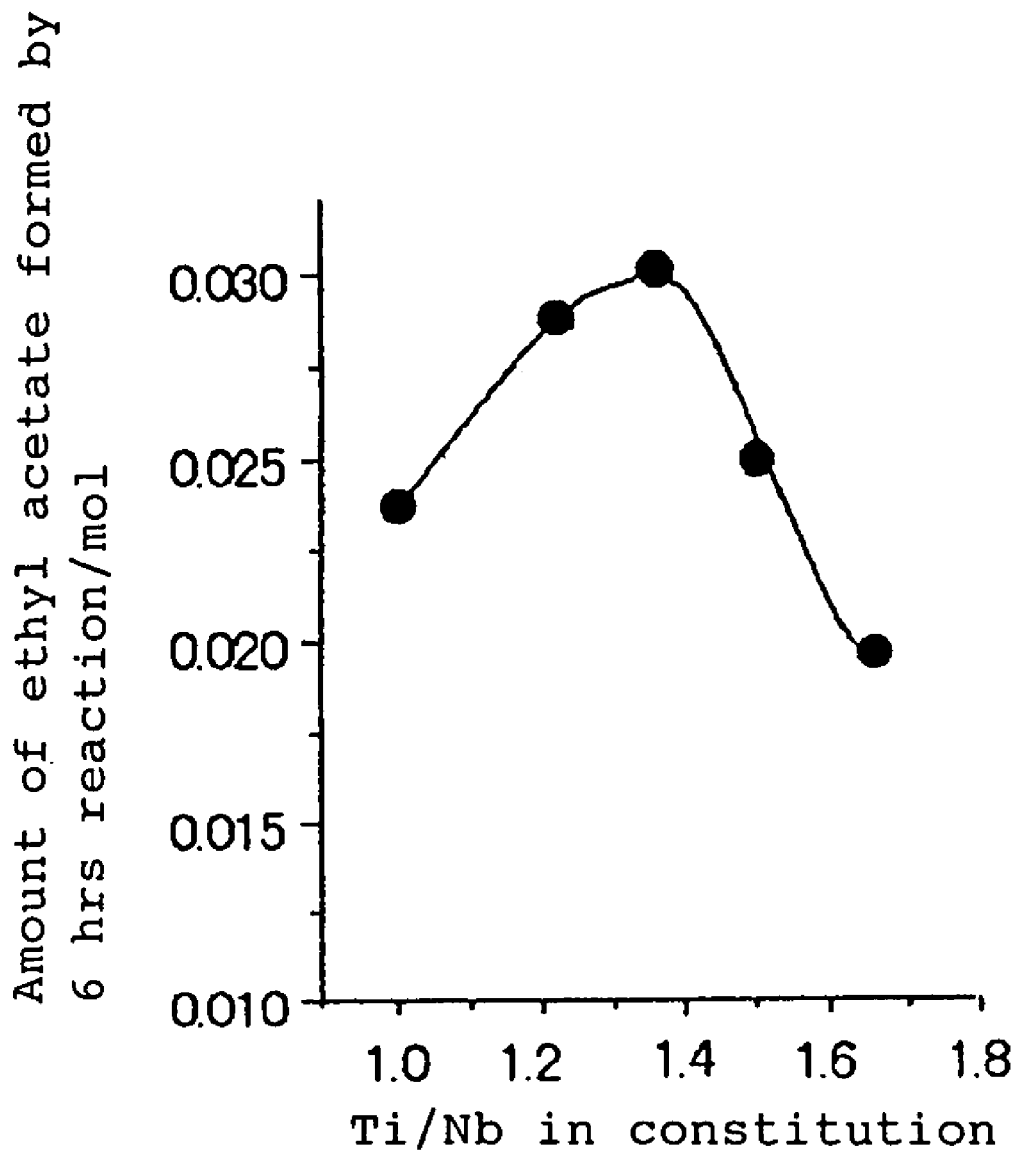
FIG. 3 indicates the relationship between catalyst activity and Ti number in catalyst composition when solid acid catalysts synthesized in Examples 1 and 2 and Comparative Examples 1 and 2 is used as an ester dehydration condensation catalyst and reacted for 6 hours.

Said $H1.1Ti_{1.1}Nb_{0.9}O_5$ sheet coagulation is vacuumed for 1 hour at 150° C., poured into mixed solution of 0.1 mol of acetic acid and 0.1 mol of ethyl alcohol under argon gas atmosphere, stirred for 6 hours at 70° C., and amount of generation of ethyl acetate formed by acid catalyst reaction is measured by a gas chromatography. Amount of ethyl acetate formed by 6 hours reaction is shown in FIG. 3. It is understood that the generating speed of ethyl acetate in $H_{1.1}Ti_{1.1}Nb_{0.9}O_5$ sheet coagulation is approximately 1.1 times larger than that of $H_{1.0}Ti_{1.0}Nb_{10}O_5$.

Example 2

Powder mixture of $K_2CO_3$, $TiO_2$, $Nb_2O_5$ is prepared by substance ratio 1.15:1.15:0.85, and lamellar metal oxide $K_{1.15}Ti_{1.15}Nb_{0.85}O_5$ is obtained by calcination of the mixture in air at 800° C. for 12 hours. The powder X-ray diffraction spectrum of $K_{1.15}Ti_{1.15}Nb_{0.85}O_5$ is shown in FIG. 2. The surface area of $K_{1.15}Ti_{1.15}Nb_{0.85}O_5$ powder is 1 $m^2g^{-1}$. Powder of lamellar metal oxide proton exchanger of $H_{1.15}Ti_{1.15}Nb_{0.85}O_5$ is obtained by dispersing 2 g of $K_{1.15}Ti_{1.15}Nb_{0.85}O_5$ powder in 200 mL of 1M nitric acid and penetrated for 14 hours then filtrated. 2 g of $H_{1.1}Ti_{1.1}Nb_{0.9}O_5$ powder is dispersed in 150 mL of distilled water and add 15 wt % aqueous solution of tetrabutylammonium hydroxide and bring the pH of the aqueous solution to 8-11 and stirred. During the stirring, pH of aqueous solution is maintained 8-11 by adding 15 wt % of aqueous solution of tetrabutylammonium hydroxide. After stirring for 24 hours, white dispersion is obtained. The obtained dispersion is centrifuged for 10 minutes by 3000 rpm and the colloidal solution of $Ti_{1.15}Nb_{0.85}O_5$ sheet to which tetrabutylammonium cation is absorbed is separated as a supernatant. When 20 mL of 0.1M nitric acid aqueous solution is added to 30 mL of colloidal solution of $Ti_{1.15}Nb_{0.85}O_5$ sheet, the colloid of $Ti_{1.15}Nb_{0.85}O_5$ sheet is precipitated and the coagulation of $H_{1.15}Ti_{1.15}Nb_{0.85}O_5$ sheet is obtained. The surface area of $H_{1.15}Ti_{1.15}Nb_{0.85}O_5$ sheet coagulation is 143 $m^2g^{-1}$.

Said $H_{1.15}Ti_{1.15}Nb_{0.85}O_5$ sheet coagulation is vacuumed for 1 hour at 150° C., poured into mixed solution of 0.1 mol of acetic acid and 0.1 mol of ethyl alcohol under argon gas atmosphere, stirred for 6 hours at 70° C., and amount of generation of ethyl acetate formed by acid catalyst reaction is measured by a gas chromatography. Amount of ethyl acetate formed by 6 hours reaction is shown in FIG. 3. It is understood that the generating speed of ethyl acetate in $H_{1.15}Ti_{1.15}Nb_{0.85}O_5$ sheet coagulation is approximately 1.3 times larger than that of $H_{1.0}Ti_{1.0}Nb_{10}O_5$.

Example 3

Powder mixture of $K_2CO_3$, $TiO_2$, $Nb_2O_5$ is prepared by substance ratio 1.2:1.2:0.8 is prepared, and lamellar metal oxide $K_{1.15}Ti_{1.15}Nb_{0.85}O_5$ is obtained by calcination of the mixture in air at 800° C. for 12 hours. The powder X-ray diffraction spectrum of $k_{1.15}Ti_{1.15}Nb_{0.85}O_5$ is shown in FIG. 2. The surface area of $K_{1.2}Ti_{1.2}Nb_{0.8}O_5$ powder is 1 $m^2g^{-1}$. Powder of lamellar metal oxide proton exchanger of $H_{1.15}Ti_{1.15}Nb_{0.85}O_5$ is obtained by dispersing 2 g of $K_{1.2}Ti_{1.2}Nb_{0.8}O_5$ powder in 200 mL of 1M nitric acid and penetrated for 14 hours then filtrated. 2 g of $H_{1.2}Ti_{1.2}Nb_{0.8}O_5$ powder is dispersed in 150 mL of distilled water and add 15 wt % aqueous solution of tetrabutylammonium hydroxide and bring the pH of the aqueous solution to 8-11 and stirred. During the stirring, pH of aqueous solution is maintained to 8-11 by adding 15 wt % of aqueous solution of tetrabutylammonium hydroxide. After stirring of 24 hours, white dispersion is obtained. The obtained dispersion is centrifuged for 10 minutes by 3000 rpm and the colloidal solution of $Ti_{1.2}Nb_{0.8}O_5$ sheet to which tetrabutylammonium cation is absorbed is separated as a supernatant. When 20 mL of 0.1M nitric acid aqueous solution is added to 30 mL of colloidal solution of $Ti_{1.2}Nb_{0.8}O_5$ sheet, the colloid of $Ti_{1.2}Nb_{0.8}O_5$ sheet is precipitated and the coagulation of $H_{1.2}Ti_{1.2}Nb_{0.8}O_5$ sheet is obtained. The surface area of $H_{1.2}Ti_{1.2}Nb_{0.8}O_5$ sheet coagulation is 110 $m^2g^{-1}$.

Said $H_{1.2}Ti_{1.2}Nb_{0.8}O_5$ sheet coagulation is vacuumed for 1 hour at 150° C., poured into mixed solution of 0.1 mol of acetic acid and 0.1 mol of ethyl alcohol under argon gas atmosphere, stirred for 6 hours at 70° C., and amount of generation of ethyl acetate formed by acid catalyst reaction is measured by a gas chromatography. Amount of ethyl acetate formed by 6 hours reaction is shown in FIG. 3.

Comparative Example 1

Powder mixture of $K_2CO_3$, $TiO_2$, $Nb_2O_5$ is prepared by substance ratio 1.0:1.0:1.0, and lamellar metal oxide $K_{1.0}Ti_{1.0}Nb_{1.0}O_5$ is obtained by calcination of the mixture in air at 800° C. for 12 hours. The powder X-ray diffraction spectrum of $K_{1.0}Ti_{1.0}Nb_{1.0}O_5$ is shown in FIG. 2. The surface area of $K_{1.0}Ti_{1.0}Nb_{1.0}O_5$ powder is 1 $m^2g^{-1}$. Powder of lamellar metal oxide proton exchanger of $H_{1.0}Ti_{1.0}Nb_{1.0}O_5$ is obtained by dispersing 2 g of $K_{1.0}Ti_{1.0}Nb_{1.0}O_5$ powder in 200 mL of 1M nitric acid and penetrated for 14 hours then filtrated. 2 g of $H_{1.0}Ti_{1.0}Nb_{1.0}O_5$ powder is dispersed in 150 mL of distilled water and add 15 wt % aqueous solution of tetrabutylammonium hydroxide and bring the pH of the aqueous solution to 8-11 and stirred. During the stirring, pH of aqueous solution is maintained 8-11 by adding 15 wt % of aqueous solution of tetrabutylammonium hydroxide. After stirring of 24 hours, white dispersion is obtained. The obtained dispersion is centrifuged for 10 minutes by 3000 rpm and the colloidal solution of $Ti_{1.0}Nb_{1.0}O_5$ sheet to which tetrabutylammonium cation is absorbed is separated as a supernatant. When 20 mL of 0.1M nitric acid aqueous solution is added to 30 mL of colloidal solution of $Ti_{1.0}Nb_{1.0}O_5$ sheet, the colloid of $Ti_{1.0}Nb_{1.0}O_5$ sheet is precipitated and the coagulation of $H_{1.0}Ti_{1.0}Nb_{1.0}O_5$ sheet is obtained. The surface area of $H_{1.0}Ti_{1.0}Nb_{1.0}O_5$ sheet coagulation is 143 $m^2g^{-1}$.

Said $H_{1.0}Ti_{1.0}Nb_{1.0}O_5$ sheet coagulation is vacuumed for 1 hour at 150° C., poured into mixed solution of 0.1 mol of acetic acid and 0.1 mol of ethyl alcohol under argon gas atmosphere, stirred for 6 hours at 70° C., and amount of generation of ethyl acetate formed by acid catalyst reaction is measured by a gas chromatography. Amount of ethyl acetate formed by 6 hours reaction is shown in FIG. 3.

Comparative Example 2

Powder mixture of $K_2CO_3$, $TiO_2$, $Nb_2O_5$ is prepared by substance ratio 1.25:1.25:0.75, and lamellar metal oxide $K_{1.25}Ti_{1.25}Nb_{0.75}O_5$ is obtained by calcining the mixture in air at 800° C. for 12 hours. The powder X-ray diffraction spectrum of $k_{1.25}Ti_{1.25}Nb_{0.75}O_5$ is shown in FIG. 2. The peak of impurity originated from $K_3Ti_5NbO_5$ at whole range becomes large, while the peak of $KTiNbO_5$ is confirmed to become small. The surface area of $K_{1.25}Ti_{1.25}Nb_{0.75}O_5$ powder is 1 $m^2g^{-1}$. Powder of lamellar metal oxide proton exchanger of $H_{1.25}Ti_{1.25}Nb_{0.75}O_5$ is obtained by dispersing 2 g of $K_{1.25}Ti_{1.25}Nb_{0.75}O_5$ powder in 200 mL of 1M nitric acid and penetrated for 14 days then filtrated. 2 g of $H_{1.25}Ti_{1.25}Nb_{0.75}O_5$ powder is dispersed in 150 mL of distilled water and add 15 wt % aqueous solution of tetrabutylammonium hydroxide and bring the pH of the aqueous solution to 8-11 and stirred. During the stirring, pH of aqueous solution is maintained 8-11 by adding 15 wt % of aqueous solution of tetrabutylammonium hydroxide. After stirring of 24 hours, white dispersion is obtained. The obtained dispersion is centrifuged for 10 minutes by 3000 rpm and the colloidal solution of $Ti_{1.25}Nb_{0.75}O_5$ sheet to which tetrabutylammonium cation is absorbed is separated as a supernatant. When 20 mL of 0.1M nitric acid aqueous solution is added to 30 mL of colloidal solution of $Ti_{1.25}Nb_{0.75}O_5$ sheet, the colloid of $Ti_{1.25}Nb_{0.75}O_5$ sheet is precipitated and the coagulation of $H_{1.25}Ti_{1.25}Nb_{0.75}O_5$ sheet is obtained. The surface area of $H_{1.25}Ti_{1.25}Nb_{0.75}O_5$ sheet coagulation is 110 $m^2g^{-1}$.

Said $H_{1.25}Ti_{1.25}Nb_{0.75}O_5$ sheet coagulation is vacuumed for 1 hour at 150° C., poured into mixed solution of 0.1 mol of acetic acid and 0.1 mol of ethyl alcohol under argon gas atmosphere, stirred for 6 hours at 70° C., and amount of generation of ethyl acetate formed by acid catalyst reaction is measured by a gas chromatography. Amount of ethyl acetate formed by 6 hours reaction is shown in FIG. 2. It is confirmed that the generating speed of ethyl acetate in $H_{1.25}Ti_{1.25}Nb_{0.75}O_5$ sheet coagulation is slower than that of $H_{1.0}Ti_{1.0}Nb_{10}O_5$. It is obvious that the impurity phase $K_3Ti_8O_{17}$ which is formed in the starting material deteriorates the acid catalyst ability.

Industrial Applicability

As mentioned above, the present invention provides the excellent effect that a solid acid catalyst which is usable for the catalyst of dehydration reaction by controlling Ti/Nb atom ratio z and number of Ti contained in titanium niobate nano-sheet coagulation. Further, these are usable as the base material with possibilities, from the view point that the multi functionality of catalyst can be easily designed by embellishing polyanion nano-sheet with different kinds of metal ion or cationic complex.

The invention claimed is:

1. A solid acid catalyst represented by $HTi_xNb_yO_5$, wherein x is $1.1<x<1.2$ and y is $0.9>y>0.8$, having a Ti/Nb atomic ratio z of $1.2<z<1.4$, obtained by proton changing of alkali metal cation of cation changeable lamellar metal oxide in which polyanion nano-sheet comprising lamellar metal oxide layers of titanium niobate lying alkali metal cation between are regularly laminated by inorganic acid or organic acid adjusted to 0.0001M to 1M, delaminating said laminated layers temporarily by inserting cation selected from the group consisting of organic amine or organic ammonium between layers of proton exchangers, preparing an aqueous colloidal solution comprising metal oxide sheets to which said organic amine or organic ammonium is absorbed, then proton exchanging said organic amine or organic ammonium by adding inorganic acid or organic acid adjusted to 0.0001M to 1M to said aqueous colloidal solution and simultaneously coagulating on titanium niobate nano-sheet.

2. The solid acid catalyst of claim 1, wherein organic amine or organic ammonium is at least one selected from the group consisting of ethylamine, propylamine or tetrabutylammonium.

3. The solid acid catalyst of claim 1, wherein the surface area of coagulated titanium niobate nano-sheet is 10 times or more to the surface area of cation changeable lamellar metal oxide proton exchanger and is in the range from 60 $m^2g^{-1}$ to 150 $m^2g^{-1}$.

4. An ester dehydration condensation catalyst comprising the solid acid catalyst of claim 2.

5. An ester dehydration condensation catalyst comprising the solid acid catalyst of claim 3.

* * * * *